United States Patent [19]
Tsuchida et al.

[11] 3,970,519
[45] July 20, 1976

[54] PROCESS FOR PRODUCING L-LEUCINE

[75] Inventors: Takayasu Tsuchida, Kawasaki; Haruo Momose, Kamakura; Yoshio Hirose, Fujisawa, all of Japan

[73] Assignee: Ajinomoto Co., Inc., Tokyo, Japan

[22] Filed: Mar. 4, 1975

[21] Appl. No.: 555,114

[30] Foreign Application Priority Data
Mar. 15, 1974 Japan................................ 49-29645

[52] U.S. Cl.................................... 195/29; 195/30; 195/47
[51] Int. Cl.².......................................... C12D 13/06
[58] Field of Search.......................... 195/29, 30, 47

[56] References Cited
UNITED STATES PATENTS

| | | | |
|---|---|---|---|
| 3,668,073 | 6/1972 | Kurihara et al........................ | 195/29 |
| 3,865,690 | 2/1975 | Okumura et al...................... | 195/29 |

*Primary Examiner*—A. Louis Monacell
*Assistant Examiner*—Robert J. Warden
*Attorney, Agent, or Firm*—Cooper, Dunham, Clark, Griffin & Moran

[57] ABSTRACT

Microorganisms of the genus Brevibacterium or Corynebacterium which resist feedback inhibition by leucine or its analogs and require at least one of isoleucine, threonine or methionine as a growth nutriment, produce L-leucine under aerobic culture conditions.

3 Claims, No Drawings

PROCESS FOR PRODUCING L-LEUCINE

BACKGROUND OF THE INVENTION

This invention relates to a process for producing L-leucine by bacterial fermentation. More particularly, it relates to a process for producing L-leucine by fermentation with mutant microorganisms of the genus Brevibacterium or Corynebacterium.

L-leucine is one of the essential amino acids. It has been used as an additive to human and animal diets and as a raw material for pharmaceutical products.

It has been reported heretofore that L-leucine can be obtained by using a microorganism which requires an amino acid such as isoleucine and methionine for its full growth (U.S. Pat. No. 3,668,073) and a mutant which is resistant to 2-thiazolealanine (British Pat. No. 1,335,210). However, the L-leucine producing ability of these known strains is generally considered to be insufficient for commercial production.

THE INVENTION

Processes have now been discovered for producing L-leucine in remarkably large quantities by fermentation. More specifically a process has been discovered for producing L-leucine which comprises culturing an L-leucine producing microorganism of the genus Brevibacterium or Corynebacterium under aerobic conditions in an aqueous medium containing a source of assimilable carbon and nitrogen, inorganic salts and nutriments at a pH or 5 to 9 until L-leucine accumulates in the medium, and recovering the accumulated L-leucine; said microorganism being characterized by:
1. requiring at least one of isoleucine, threonine or methionine as a growth nutriment, and
2. being resistant to feedback inhibition by leucine and analogs of leucine.

The presently preferred L-leucine producing microorganisms are artificially produced mutants of strains of Brevibacterium and Corynebacterium obtained by conventional mutant inducing procedures utilizing irradiation by X-rays or ultraviolet light or chemical treatment with nitrosoquanidine, diethyl sulfate or diethyl nitrite. The preferred strains for producing such mutants are Brevibacterium lactofermentum and Corynebacterium glutamicum. As aforesaid the useful microorganisms are identified by screening for requirements of isoleucine, threonine or methionine and for resistance to feedback inhibition by leucine and its analogs.

The microorganisms useful in the invention can be isolated by the replica method from growth colonies on the plate according to specific nutrient requirements, which are determined by standard methods known in the art. The mutant strains having resistance to feedback inhibition and/or repression of leucine can be isolated from the parent strains and identified by resistance to feedback by leucine or analogs such as β-hydroxyleucine, trifluoroleucine, 2-thiazolealanine, 2-amino-4-methyl-hexanoic acid, glycylleucine, α-aminobutyric acid, β-hydroxyvaline, thiaisoleucine. The compounds 2-thiazoleanaline and β-hydroxyleucine are particularly useful for such screening.

Particularly suitable mutant strains for use in the process according to the present invention are Brevibacterium lactofermentum AJ-3718 (FERM-P 2516) which is resistant to 2-thiazolealanine and β-hydroxyleucine and requires isoleucine and methionine, Brevibacterium lactofermentum AJ-3452 (FERM-P 1965) which is resistant to 2-thiazolealanine and β-hydroxyleucine and requires threonine, and Brevibacterium lactofermentum AJ-3719 (FERM-P 2517) which is resistant to 2-thiazolealamine and β-hydroxyleucine and requires isoleucine and methionine. These three mutants were all derived from the parent strain Brevibacterium lactofermentum ATCC 13869. Corynebacterium glutamicum AJ-3453 (FERM-P 1966) which is resistant to 2-thiazolealanine and β-hydroxyleucine and requires isoleucine, Corynebacterium glutamicum AJ-3455 (FERM-P 1968) which is resistant to 2-thiazolealamine and β-hydroxyleucine and requires threonine, and Corynebacterium glutamicum AJ-3720 (FERM-P 2518) which is resistant to 2-thiazolealeanine and β-hydroxyleucine and requires isoleucine (all of which were derived from Corynebacterium glutamicum ATCC 13032) are also particularly useful in this process.

The FERM-P number shown herein is the deposit accession number of the Fermentation Research Institute, Agency of Industrial Science of Technology, the Ministry of the Industrial Trade and Industry, Japan.

Conventional culture mediums may be used to produce L-leucine in accordance with the present invention. These normally include sources of assimilable carbon and nitrogen and the usual minor constituents such as inorganic salts and organic nutrients. Examples of the carbon source are carbohydrates glucose, fructose, maltose, starch hydrolysate, cellulose hydrolysate or molasses, organic acids such as acetic, propionic or succinic, alcohols such as glycerol, methanol or ethanol, any hydrocarbons such as n-paraffin. Useful nitrogen sources include ammonium sulfate, urea, ammonium nitrate, ammonium chloride or gaseous ammonia. Inorganic salts, such as phosphates, magnesium, calcium, ferrous, manganese and other minor metallic salts are generally present. Amino acids, vitamins, "Aji-Eki" (Brand Name of soybean protein hydrolysate), yeast extracts, peptone and casamino acid are preferably employed for good bacterial growth. Of course, isoleucine, threonine or methionine will be utilized.

The fermentation of the present invention is performed at a pH of from 5 to 9, at a temperature of 24° to 37°C under aerobic conditions for 2 to 7 days or until sufficient L-leucine accumulates. The pH of the culture medium can be adjusted by adding sterile calcium carbonate, urea, aqueous or gaseous ammonia, mineral acid or organic acid during the fermentation.

The L-leucine is recovered from the cultured broth by conventional methods. It may be identified by its RF values in paper chromatography, its ninhydrin reaction and by bioassay with Leuconostoc mesenteroides ATCC 8042.

The following experiment shows the difference in degree of feedback inhibition and repression by leucine analogue between the mutant strains employed in the present process and strains which do not have resistance to leucine analogues. It illustrates one of the steps employed in identifying microorganisms useful in this invention.

EXPERIMENT

1. A culture medium containing 10% glucose, 4% $(NH_4)_2SO_4$, 0.1% $KH_2PO_4$, 0.04% $MgSO_4 \cdot 7H_2O$, 2ppm $Fe^{++}$, 2ppm $Mn^{++}$, 100γ/l biotin, 350γ/l thiamine hydrochloride, 2ml/dl soybean protein hydrolyzate and 5% $CaCO_3$ (sterilized separately), at pH 7.0 was prepared, 20ml aliquots of the medium were each placed in 500ml shaking flasks, and autoclaved at 110°C for 5 minutes. The media were supplemented with required nutrients as shown in Table 1, and were respectively inoculated with the seven strains listed in the table and cultured at 31°C for 24 hours. The strains had been cultured previously on a bouillon slant at 30°C for 24 hours. The microbial cells obtained from the broth after 24 hours' cultivation were examined according to the modified method of Burns et al (J. Bacteriol, 91, 1570–1576, 1966) to determine how the activity of α-isopropylmalate synthetase was influenced by the presence or absence of L-leucine. Specifically, the cells were harvested, washed twice with 0.05M tris (hydroxymethyl) amino methane-HCl (pH 7.2) buffer, and suspended in the same buffer. The suspended cells were disrupted by treatment with a 10-KC sonic Oscillator (Tōyō-Rikō Type 50-S, 80W) for 30 min. The cell debris was removed by centrifugation at 13,000 g. Dialyzed crude extracts were prepared by dialyzing 10ml of the supernatant from the centrifugation in viscose tubing against 1000ml of the same buffer for 16 hours at 4°C with stirring. These dialyzed crude extracts were assayed for α-isopropylmalate synthetase activity. The mixture for determining activity contained (in 0.5ml); sodium α-ketoisovalerate, 5 μmoles; acetyl CoA, 0.5 μmoles; tris (hydroxymethyl) aminomethane-HCl (pH 8.5), 50 μmoles; potassium chloride, 35 μmoles; and dialyzed crude extract. After 8 min. at 30°C, the reaction was stopped by adding 3.0ml of 0.2% metaphosphoric acid in saturated sodium chloride. Acetyl CoA cleavage was determined by using the 5,5'-dithiobis-2-nitrobenzoic acid assay of Srere and Brazil for free —SH groups [Srere, P., Brazil, H. and Gonen, L., Acta. Chem. Scand., 17, S129 (1963)].

The 5,5'-dithiobis-2-nitrobenzoic acid assay was standardized with CoA. A reaction mixture from which α-ketoisovalerate had been omitted served to correct for the acetyl CoA cleavage due to other activities in the dialyzed crude extracts.

One activity unit was defined as that amount of enzyme which catalyzes the formation of 1 μmole of CoA per hour under the standard assay conditions. The specific activity was expressed in units per mg of protein.

Protein concentration was determined by the method of Lowry et al., [Lowry, O. H., N. J. Rosebrough; A. L. Farr, and R. J. Randall, J. Biol. Chem., 193, 265 (1951)].

The results are shown in Table 1 from which it is apparent that the α-isopropylmalate synthetase of the preferred strains of this invention are resistant to feedback inhibition by L-leucine.

Table 1

| Strains employed | Amino Acids added to the medium | | Specific activity | |
|---|---|---|---|---|
| | Amino Acids | Amount (mg/dl) | Without Leu. | With Leu. |
| Brevibacterium Lactofermentum FERM-P 1841 | threonine | 20 | 100 | 50 |
| Brevibacterium Lactofermentum FERM-P 1858 | isoleucine & methionine | 10 10 | 100 | 65 |
| Brevibacterium Lactofermentum FERM-P 2516 | isoleucine & methionine | 10 10 | 100 | 95 |
| Brevibacterium Lactofermentum FERM-P 1965 | threonine & isoleucine | 20 20 | 100 | 98 |
| Brevibacterium Lactofermentum FERM-P 2517 | methionine | 30 | 100 | 100 |
| Corynebacterium glutamicum ATCC 13032 | isoleucine | — | 100 | 40 |
| Corynebacterium glutamicum FERM-P 1966 | threonine | — | 100 | 98 |

2. The repressive effects of L-leucine on α-isopropylmalate synthetase in leucine producers were examined according to the modified method of Burns et al.

The strains of Table 1 were separately innoculated in each of the following media:
a. The amino acid supplemented medium of Table 1.
b. The same medium containing an additional 0.2% L-leucine by weight.
c. The same medium containing an additional 0.5% L-leucine by weight.

Each innoculum was cultured for 24 hours at 30°C. The activity was determined as explained above in connection with Table 1. The results are shown in Table 2.

Table 2

| Strains employed | Amount of Leu. Specific Activity | | |
|---|---|---|---|
| | 0 | 0.2 % | 0.5 % |
| Brevibacterium lactofermentum FERM-P 1841 | 1.80 | 0.70 | 0.48 |
| Brevibacterium lactofermentum FERM-P 1858 | 2.00 | 0.81 | 0.30 |
| Brevibacterium lactofermentum FERM-P 2516 | 5.00 | 4.90 | 4.85 |
| Brevibacterium lactofermentum FERM-P 1965 | 4.51 | 4.25 | 4.26 |
| Brevibacterium lactofermentum FERM-P 2517 | 4.80 | 4.75 | 4.70 |
| Corynebacterium glutamicum ATCC 13032 | 2.25 | 0.28 | 0.05 |
| Corynebacterium glutamicum FERM-P 1966 | 3.80 | 3.35 | 3.34 |

It is apparent that the α-isopropylmalate activity of the preferred mutants of this invention is not significantly repressed even in the presence of large amounts of leucine.

The following non-limiting example is illustrative of the invention.

EXAMPLE 1

A culture medium containing 10% glucose, 4% $(NH_4)_2SO_4$, 0.1% $KH_2PO_4$, 0.04% $MgSO_4 \cdot 7H_2O$, 2ppm $Fe^{++}$, 2ppm $Mn^{++}$, 100γ/l biotin, 350γ/l thiamine hydrochloride, 2 ml/dl soybean protein hydrolysate, and 5% $CaCO_3$ (sterilized separately, at pH 7.0 was prepared, 20ml aliquots of the medium were placed in 500 ml shaking flasks, and autoclaved at 100°C for 5 minutes.

The media were supplemented with the required amino acids as listed in Table 3, and were thereafter inoculated with strains shown in the table.

After 72 hours' cultivation at 30°C, each culture broth was found to contain L-leucine in amounts shown.

Table 3

| Strains employed | Resistance | Amino Acids | Amino Acids Required Amount (mg/dl) | L-leucine Produced (g/dl) |
|---|---|---|---|---|
| Brevibacterium lactofermentum FERM-P 1841 | — | Threonine | 20 | 0 |
| Brevibacterium lactofermentum FERM-P 1858 | — | Isoleucine & Methionine | 10 / 10 | 0 |
| Brevibacterium lactofermentum FERM-P 2516 | 2-TA, β-HL | Isoleucine & Methionine | 10 / 10 | 2.21 |
| Brevibacterium lactofermentum FERM-P 1965 | 2-TA, β-HL | Threonine | 20 | 2.10 |
| Brevibacterium lactofermentum FERM-P 2517 | 2-TA, β-HL | Isoleucine & Methionine | 20 / 30 | 2.20 |
| Coryne. glutamicum ATCC 13032 | — | Isoleucine | — | 0 |
| Coryne. glutamicum ATCC 14296 | — | Threonine | — | 0 |
| Coryne. glutamicum FERM-P 1966 | 2-TA, β-HL | Isoleucine | 15 | 1.80 |
| Coryne. glutamicum FERM-P 1968 | 2-TA, β-HL | Threonine | 15 | 1.70 |
| Coryne. glutamicum FERM-P 2518 | 2-TA, β-HL | Isoleucine | 15 | 1.95 |

Table 3-continued

| Strains employed | Resistance | Amino Acids | Amino Acids Required Amount (mg/dl) | L-leucine Produced (g/dl) |
|---|---|---|---|---|
| micum FERM-P 2518 | β-HL | | | |

Note:
2-TA: 2-Thiazolcalanine
β-HL: β-Hydroxyleucine

What is claimed is:
1. A process for producing L-leucine which comprises cultivating a microorganism selected from the group consisting of *Brevibacterium lactofermentum* FERM-P 2516, 2517 and 1965 and *Corynebacterium glutamicum* FERM-P 1966, 1968 and 2518 in an aqueous medium containing a source of assimilable carbon and nitrogen, inorganic salts and nutriments at a pH of 5 to 9 until L-leucine accumulates in the medium, and recovering the accumulated L-leucine.
2. A process as in claim 1 wherein said microorganism is *Brevibacterium lactofermentum* FERM-P 2516, 2517 or 1965.
3. A process as in claim 1 wherein said microorganism is *Corynebacterium glutamicum* FERM-P 1966, 1968 or 2518.

* * * * *